United States Patent [19]

Alker et al.

[11] Patent Number: 4,568,677

[45] Date of Patent: Feb. 4, 1986

[54] 2-(4-PYRIMIDONE ALKOXYALKYL) DIHYDROPYRIDINE ANTI-ISCHAEMIC AND ANTIHYPERTENSIVE AGENTS

[75] Inventors: David Alker, Eastry, Nr. Deal; Peter E. Cross, Canterbury; Simon F. Campbell, Deal, all of England

[73] Assignee: Pfizer Inc., New York, N.Y.

[21] Appl. No.: 623,265

[22] Filed: Jun. 21, 1984

[30] Foreign Application Priority Data

Jul. 23, 1983 [GB] United Kingdom ............... 8319886
Jan. 7, 1984 [GB] United Kingdom ............... 8400354

[51] Int. Cl.[4] .................. C07D 401/12; C07D 401/14; C07D 413/14; A61K 31/505

[52] U.S. Cl. ..................................... 514/272; 514/236; 514/269; 544/123; 544/300

[58] Field of Search ............... 544/239, 240, 316, 319, 544/365, 405, 123, 300; 424/250, 251; 514/236, 272, 269

[56] References Cited

U.S. PATENT DOCUMENTS 4,430,333  2/1984  Campbell et al. ................... 546/321

FOREIGN PATENT DOCUMENTS 100189  2/1984  European Pat. Off. ............ 546/321

OTHER PUBLICATIONS

Chemical Abstracts, 101: 110954a.
Schramm, M. et al, "Novel Dihydropyridines with Positive Inotropic Action", Nature, vol. 303, Jun. 9, 1983, pp. 535-537.
Bossert, F. et al, "4-Aryldihydropyridines", Angew. Chem. Int., Ed. Engl., 20, (1981) pp. 762-769.

Primary Examiner—Henry H. Jiles
Assistant Examiner—Dale A. Bjorkman
Attorney, Agent, or Firm—Charles J. Knuth; Albert E. Frost; James M. McManus

[57] ABSTRACT 1,4-Dihydropyridine derivatives of the formula:

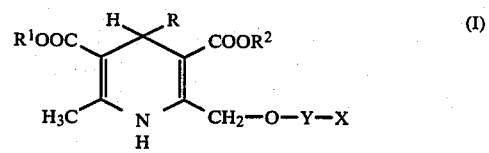

wherein R is aryl or heteroaryl; $R^1$ and $R^2$ are each independently $C_1$-$C_4$ alkyl or 2-methoxyethyl; X is a 5 or 6 membered nitrogen-containing heterocyclic ring which is substituted with one or more hydroxyl or oxo groups and which may optionally be fused to a further 5 or 6 membered nitrogen-containing heterocyclic ring, and which may optionally be further substituted in the heterocyclic ring or further fused heterocyclic ring; Y is $-(CH_2)_n-$, $-CH_2CH(CH_3)-$ or $-CH_2C(CH_3)_2-$; and n is 1 to 3 when X is linked to Y by a ring carbon atom, or 2 or 3 when X is linked to Y by a ring nitrogen atom; and their pharmaceutically acceptable salts, and pharmacuetical preparation containing such compounds, have utility as anti-ischaemic and antihypertensive agents.

6 Claims, No Drawings

2-(4-PYRIMIDONE ALKOXYALKYL) DIHYDROPYRIDINE ANTI-ISCHAEMIC AND ANTIHYPERTENSIVE AGENTS

BACKGROUND OF THE INVENTION

This invention relates to certain dihydropyridines, specifically to certain 1,4-dihydropyridines having a hydroxy or oxo-substituted heterocyclic ring in a side chain attached to the 2-position, which have utility as anti-ischaemic and antihypertensive agents, and to pharmaceutical preparations containing such compounds.

The compounds of the invention reduce the movement of calcium into the cell and they are thus able to delay or prevent the cardiac contracture which is believed to be caused by an accumulation of intracellular calcium under ischaemic conditions. Excessive calcium influx during ischaemia can have a number of additional adverse effects which would further compromise the ischaemic myocardium. These include less efficient use of oxygen for ATP production, activation of mitochondrial fatty acid oxidation and possibly, promotion of cell necrosis. Thus the compounds are useful in the treatment or prevention of a variety of cardiac conditions, such as angina pectoris, cardiac arrythmias, heart attacks and cardiac hypertrophy. The compounds also have vasodilator activity since they can inhibit calcium influx in cells of vascular tissue and they are thus also useful as antihypertensive agents and for the treatment of coronary vasospasm.

According to the specification of our European Patent Application No. 60674 there are described and claimed a number of dihydropyridine anti-ischaemic and antihypertensive agents wherein the 2-position of the dihydropyridine ring is substituted with certain N,N-disubstituted-aminoalkoxymethyl groups. Our copending European patent application No. 100189 describes and claims a related series of compounds wherein the 2-position is substituted with an aromatic heterocyclylalkoxymethyl group. We have now discovered a further series of dihydropyridine compounds having valuable therapeutic properties wherein the 2-position substituent bears a hydroxy- or oxo-substituted heterocyclic group.

Thus according to the invention, there are provided novel 1,4-dihydropyridine derivatives of the formula:

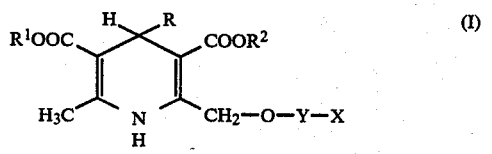

and their pharmaceutically acceptable salts; wherein
R is aryl or heteroaryl;
$R^1$ and $R^2$ are each independently $C_1$–$C_4$ alkyl or 2-methoxyethyl;
X is a 5 or 6 membered nitrogen-containing heterocyclic ring which is substituted with one or more hydroxyl or oxo groups and which may optionally be fused to a further 5 or 6 membered nitrogen-containing heterocyclic ring, and which may optionally be additionally substituted in the heterocyclic ring or further fused heterocyclic ring by one or more $C_1$–$C_4$ alkyl, phenyl, CN, $N(R^3)_2$, $(CH_2)_m CO_2 R^3$ or $(CH_2)_m CON(R^3)_2$ groups, wherein each $R^3$ is independently H or $C_1$–$C_4$ alkyl or the two groups $R^3$ are taken together with the nitrogen atom to which they are attached to form a pyrrolidinyl, piperidino, morpholino, piperazinyl or N-($C_1$–$C_4$ alkyl)-piperazinyl group, and m is 0 or 1; Y is —$(CH_2)_n$—, —$CH_2CH(CH_3)$— or —$CH_2C(CH_3)_2$—; and
n is 1 to 3 when X is linked to Y by a ring carbon atom, or 2 or 3 when X is linked to Y by a ring nitrogen atom.

The pharmaceutically acceptable acid addition salts of the compounds of the formula (I) are those formed from acids which form non-toxic acid addition salts, for example the hydrochloride, hydrobromide, sulphate or bisulphate, phosphate or acid phosphate, acetate, citrate, fumarate, gluconate, lactate, maleate, succinate and tartrate salts. For compounds with an acidic substituent salts may also be formed with bases, examples are the sodium, potassium and ammonium salts.

The term "aryl" as used in this specification for R, includes phenyl and phenyl substituted by one or two substituents each independently selected from nitro, halo, $C_1$–$C_4$ alkyl, $C_1$–$C_4$ alkoxy, hydroxy, trifluoromethyl and cyano. It also includes 1- and 2-naphthyl.

The term "heteroaryl" as used in this specification for R means an aromatic heterocyclic group which may optionally be substituted and includes, for example, benzofuranyl; benzothienyl; pyridyl optionally substituted by methyl, methylthio, cyano or halo; quinolyl; benzoxazolyl; benzothiazolyl; furyl; pyrimidinyl; thiazolyl; 2,1,3-benzoxadiazol-4-yl; 2,1,3-benzothiadiazol-4-yl; and thienyl optionally monosubstituted by halo or $C_1$–$C_4$ alkyl.

The 5 or 6 membered nitrogen-containing heterocyclic ring X may contain from one to three nitrogen atoms in the ring and may be saturated or unsaturated. As will be understood by those skilled in the art the hydroxyl- or oxo-substituted heterocyclic rings can be subject to keto-enol tautomerism and the group may be present either as a free hydroxyl group when in the tautomeric enol form, or as an oxo group when in the keto form. Which particular isomer is present in normal circumstances can be readily determined by appropriate physical measurements, such as for example by infra-red spectroscopy, and, in some instances the compounds may exist as mixtures of the two forms. However it is to be understood that the invention includes both forms of the compounds where they can exist and, in the description and Examples hereto, references to the hydroxy or keto form of the compound include all possible tautomeric forms and are not necessarily to be taken to indicate which is the predominant tautomeric form of the compound.

The ring X may be linked to the group Y either by a ring carbon or a ring nitrogen atom, with the proviso that, if X is linked by a ring nitrogen atom, Y must contain at least two carbon atoms (i.e. n is 2 or 3).

Examples of suitable heterocyclic rings include 2-,4- and 5-imidazolone, 3-pyrazolone, pyrroline-2,5-dione, imidazolidine-2,4-dione, 2-pyridone, 3-piperazinone, 4-pyrimidone, pyrimidine-2,4-dione, 5-hydroxy-(1H)-1,2,3-triazole and 1-oxo-1,3-dihydropyrrolo[2,3b]pyridine.

The heterocyclic ring X may contain further substituents. Preferred substituent groups are amino, lower alkyl, particularly methyl, carbamoyl and CN. Thus particular and preferred examples of X include 1-(2-amino-4-imidazolone), 1-(imidazolidine-2,4-dione), 1-(4- amino-2-imidazolone), 2-(1-oxo-1,3-dihydropyr-rolo[2,3b]pyridine), 6-(2-amino-4-pyrimidone) and 6-(2,3-dimethyl-4-pyrimidone).

The term "halo" means fluoro, chloro, bromo or iodo. Alkyl and alkoxy groups having 3 or more carbon atoms can be straight or branched chain. Compounds containing asymmetric centres will exist as one or more pairs of enantiomers and the invention includes the separated d- and l-optically active isomers as well as mixtures thereof.

Preferred values for R are 2-chlorophenyl and 2,3-dichlorophenyl. $R^1$ and $R^2$ are preferably $CH_3$ or $C_2H_5$; the case where $R^1$ is $CH_3$ and $R^2$ is $C_2H_5$ being especially preferred. Y is preferably $-(CH_2)_2-$ when X is linked to Y by a ring nitrogen atom, or $-CH_2-$ when X is linked to Y by a ring carbon atom. Thus particular and preferred examples of compounds of the invention include the following:

2-Amino-1-{2-<[4-(2,3-dichlorophenyl)-3-ethoxycarbonyl-5-methoxycarbonyl-6-methyl-1,4-dihydropyridin-2-yl]methoxy>ethyl}-4-imidazolone;

1-{2-<[4-(2,3-Dichlorophenyl)-3-ethoxycarbonyl-5-methoxycarbonyl-6-methyl-1,4-dihydropyridin-2-yl]methoxy>ethyl}imidazolidine-2,4-dione;

4-Amino-1-{2-<[4-(2,3-dichlorophenyl)-3-ethoxycarbonyl-5-methoxycarbonyl-6-methyl-1,4-dihydropyridin-2-yl]methoxy>ethyl}-2-imidazolone;

2-{2-<[4-(2,3-Dichlorophenyl)-3-ethoxycarbonyl-5-methoxycarbonyl-6-methyl-1,4-dihydropyridin-2-yl]methoxy>ethyl}-1-oxo-1,3-dihydropyrrolo[2,3-b]pyridine;

6-{[4-(2,3-Dichlorophenyl)-3-ethoxycarbonyl-5-methoxycarbonyl-6-methyl-1,4-dihydropyridin-2-yl]methoxymethyl}-2,3dimethyl-4-pyrimidone, and 2-Amino-6-{[4-(2,3-dichlorophenyl)-3-ethoxycarbonyl-5-methoxycarbonyl-6-methyl-1,4-dihydropyridin-2-yl]methoxymethyl}-4-pyrimidone the latter compound being particularly preferred as having especially favourable properties.

DETAILED DESCRIPTION OF THE INVENTION

The compounds of the invention can be prepared by a number of different processes according to the invention.

(a) In one process the compounds of formula I can be prepared by the Hantzsch synthesis, according to the following reaction scheme:

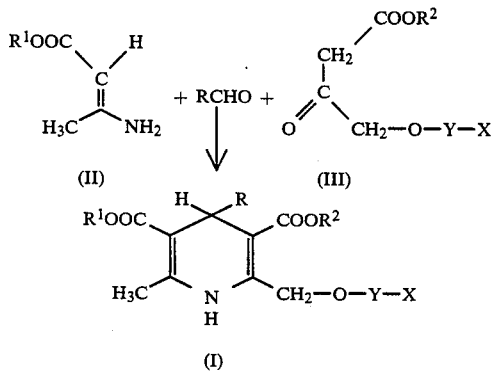

wherein R, $R^1$, $R^2$, X and Y are as previously defined.

In a typical procedure, the ketoester (III) and aldehyde are heated under reflux in a suitable organic solvent, e.g. a $C_1$–$C_4$ alkanol such as ethanol, for about 15 minutes, and then the aminocrotonate (II) is added. Alternatively the aminocrotonate (II), the ketoester (III) and the aldehyde can be heated together in the solvent. Preferably a small amount of a lower alkanoic acid such as acetic acid is added to neutralise the solution. The resulting solution can then be heated at 60°–130° C., preferably under reflux, until the reaction is essentially complete, typically in 24 hours or less. The product of the formula (I) is then isolated and purified by conventional procedures, for example by partition, recrystallisation or by chromatography.

The ketoesters (III) are either known compounds or they can be prepared by methods analogous to those of the prior art, such as for example the method of Troostwijk and Kellogg, J.C.S. Chem. Comm., 1977, page 932, or using the methods illustrated in European Patent application No. 60674. Similarly the amino-crotonates (II) and the aldehydes are either known or can be prepared by known methods in accordance with literature precedents.

(b) In an alternative variation of the Hantzsch synthesis the compounds of formula (I) can be prepared by the following process:

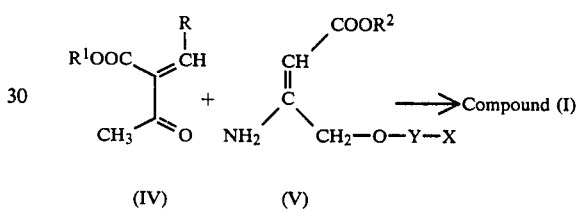

The crotonate (V) is typically prepared in situ by reaction of the corresponding ketoester (III) with ammonium acetate by refluxing in a suitable organic solvent, e.g. a $C_1$–$C_4$ alkanol such as ethanol, for up to an hour. The crotonate (V) is then reacted with compound (IV), typically by heating in the solvent for up to about 5 hours at temperatures of from 60° to 130° C. The product (I) can then be isolated and purified by conventional procedures as before.

The starting materials (IV) are again either known compounds or they may be prepared by methods analogous to those of the prior art in accordance with literature precedents, see for example Can. J. Chem., 1967, 45, 1001.

It will be appreciated that while all the compounds of the invention may be prepared by the processes described under (a) or (b) above, in many cases particular compounds may more conveniently be prepared starting with the preformed dihydropyridine. Such processes are within the knowledge and skill of those versed in the art and will vary according to the nature of the heterocyclic ring X desired. The following processes describe examples of a number of processes for preparing the compounds of formula (I) containing particular heterocyclic rings but other alternatives and variations will be readily evident to those skilled in the art.

(c) Thus in a further process compounds of the formula (I) wherein X is a 4-pyrimidone or 3-pyrazolone group may be prepared from the corresponding dihydropyridine ketoester of formula:

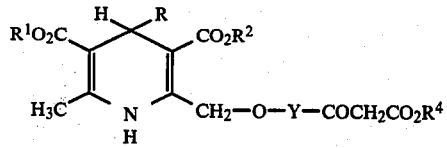

wherein R, $R^1$, $R^2$ and Y are as previously defined and $R^4$ is $C_1$–$C_4$ lower alkyl, by reacting either with a compound of the formula:

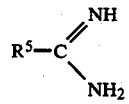

wherein $R^5$ is $N(R^3)_2$, $C_1$–$C_4$ alkyl or phenyl, where $R^3$ is as previously defined, to give compounds wherein X is a 2-substituted-4-pyrimidone group; or with hydrazine to give compounds wherein X is a 3-pyrazolone group.

Thus reaction of the compound of formula (VI) with guanidine (VIa; $R^5$=$NH_2$) yields the corresponding compound of formula (I) wherein X is 2-amino-4-pyrimidon-6-yl. Similarly reaction with acetamidine (VIa; $R^5$=$CH_3$) gives the corresponding compound of formula (I) wherein X is 2-methyl-4-pyrimidon-6-yl. The reaction in each case is performed with the reactants dissolved in an organic solvent, e.g. ethanol, in the presence of an organic base. Several days at room temperature may be required before the reaction is substantially complete and the product is then isolated conventionally using normal extraction, washing and evaporation techniques, and purified, if necessary, by recrystallisation or by chromatography.

The reaction can also be performed in a similar manner using hydrazine hydrate to give the compound of formula (I) wherein X is a 5-(3-pyrrazolone) group.

A further variant of this process can also be used to prepare certain compounds of the formula (I) wherein X is a bicyclic system incorporating a pyrimidone ring. Thus, for example, reaction of a compound of the formula (VI) with 2-aminoimidazolium sulphate gives the compound of formula (I) wherein X is a 7-(5-hydroxyimidazo[1,2-a]pyrimidine) group. Similarly, reaction with 2-iminopiperidine gives the compound where X is a 4-oxo-tetrahydropyrido[1,2-a]pyrimidine group.

Simple transformation reactions can of course be applied to the final products to introduce or modify substituent groups in accordance with conventional and well known procedures. Thus methylation, for example using iodomethane in the presence of a base, can be used to prepare the compound of formula I wherein X is 2-amino-3-methyl-4-pyrimidone from the corresponding 2-amino-4-pyrimidone. Similarly treatment of the compound of formula I wherein X is 2-methyl-4-pyrimidone with iodomethane yields the corresponding compound where X is 2,3-dimethyl-4-pyrimidone.

The ketoester starting materials of formula (VI) are prepared from the corresponding (1,4-dihydropyridin-2-yl)methoxy alkanoic acid by standard procedures. Thus one route that we have employed is to react the imidazolide derivative of the acid with the sodium salt prepared from 2,2-dimethyl-1,3-dioxane-4,6-dione with sodium hydride. Ring opening of the product is effected by heating in a lower alkanol to yield the desired ketoester. The amidines and guanidines of formula (VIa) are known compounds.

(d) In a further process, compounds wherein X is a 1-(2-amino-4-imidazolone) group are prepared from a compound of the formula:

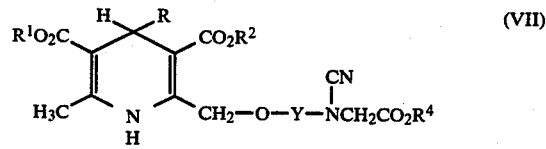

wherein R, $R^1$, $R^2$, $R^4$ and Y are as previously defined, by reacting with ammonia. The reaction is readily performed by adding the compound of formula (VII) to a saturated solution of methanolic ammonia. After several hours at room temperature the solvent is evaporated to yield the desired product.

The starting materials of formula (VII) are prepared from the corresponding 2-[(N-alkoxycarbonylmethyl)amino]alkoxymethyl-1,4-dihydropyridines by reacting with cyanogen bromide in chloroform for several hours at room temperature.

(e) In a further process, compounds wherein X is a 1-(imidazolidine-2,4-dione) group or a 1-(4-amino-2-imidazolone) group which may be substituted on the 3- or 5-positions with lower alkyl groups are prepared from compounds of the formula:

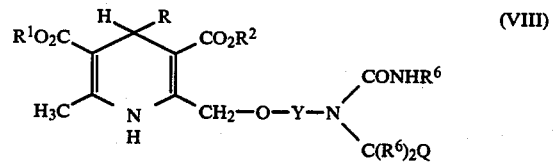

wherein R, $R^1$, $R^2$ and Y are as previously defined, each $R^6$ is independently H or $C_1$–$C_4$ alkyl and Q is $CO_2$($C_1$–$C_4$ alkyl) or CN; by reaction with a base.

The base catalysed ring closure occurs readily and is conveniently achieved by, for example, adding sodium hydride to a suspension of the compound (VIII) in a lower alkanol, and stirring for one to two hours at room temperature. The solvent is removed and the product purified by conventional techniques. Thus reaction of the compound of formula (VIII) wherein each $R^6$ is hydrogen and Q is $CO_2C_2H_5$ with base yields the compound of formula (I) wherein X is imidazolidin-2,4-dion-1-yl. Similarly reaction of the compound wherein each $R^6$ is hydrogen and Q is CN gives the compound of formula (I) wherein X is 4-amino-2-imidazolon-1-yl.

The urea starting materials of formula (VIII) wherein Q is $CO_2$($C_1$–$C_4$ alkyl) are prepared as described in our co-pending European Patent application No. 84301452.3 from the corresponding 2-[(N-alkoxycarbonylmethyl)amino]alkoxymethyl)-dihydropyridine by reaction with an isocyanate.

The compounds of formula (VIII) wherein Q is CN are prepared from the corresponding 2-[(N-cyanomethyl)amino]alkoxymethyl-1,4-dihydropyridines by reaction with isocyanates.

(f) The compounds of formula (I) wherein X is a 1-(5-amino-2-imidazolone) or a 1-(imidazolidine-2,5-dione) group are prepared in a similar manner to the processes described under (d) and (e) above but starting with a compound of the formula:

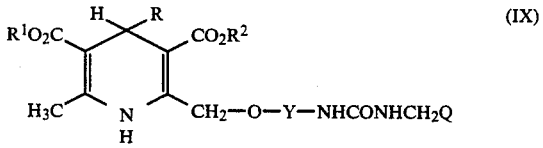

wherein R, R$^1$, R$^2$, Q and Y are as previously defined.

Thus in the case where Q is CO$_2$(C$_1$–C$_4$ alkyl), the cyclisation is effected by stirring the compound of formula (IX) in methanolic ammonia at room temperature for several hours, typically overnight, to yield the product wherein X is imidazolidin-2,5-dion-1-yl.

Alternatively, when Q is CN, the cyclisation can be effected for example in methanol with sodium methoxide at room temperature for an hour or so, to yield the compound of formula (I) wherein X is a 1-(5-amino-2-imidazolone) group.

The starting materials of formula (IX) are again prepared from the corresponding 2-(aminoalkoxymethyl)-1,4-dihydropyridines by reaction either with carbonyldiimidazole followed by reacting with aminoacetonitrile to give the compound of formula (IX) wherein Q is CN, or with an alkoxycarbonylmethyl isocyanate to give the compound wherein Q is CO$_2$(C$_1$–C$_4$ alkyl).

(g) The compounds of formula (I) wherein X is a 2-methyl-5-imidazolone group are prepared from the corresponding 2-(aminoalkoxymethyl)-1,4-dihydropyridine by reacting with ethyl N-(ethoxycarbonylmethyl)acetimidate according to the following reaction scheme:

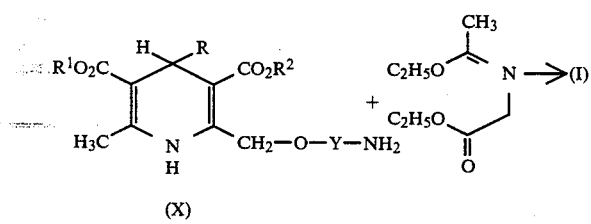

The reaction occurs at room temperature and is conveniently effected by stirring a solution of the reactants in a lower alkanol solvent, e.g. ethanol, for several hours.

(h) The compounds of formula (I) wherein X is a 4-ethoxycarbonyl-5-hydroxy-(1H)-1,2,3-triazole group are prepared from the corresponding 2-azidoalkoxymethyl-1,4-dihydropyridine of formula:

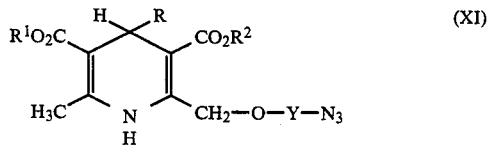

wherein R, R$^1$, R$^2$ and Y are as previously defined by reacting with diethyl malonate in the presence of a base. The reaction is conveniently effected by heating the reactants in a lower alkanolic solvent to which sodium hydride has been added and a period of up to 24 hours under reflux is generally sufficient to complete the reaction. The product is isolated and purified using conventional procedures.

The azido starting materials of formula (XI) and amines of formula (X) are prepared as described in European Patent Application Publication No. 89167.

(i) The compounds of formula (I) wherein X is a 2-(1-oxo-1,3-dihydropyrrolo[2,3-b]pyridine) group are prepared from the corresponding 2-(aminoalkoxymethyl)-1,4-dihydropyridines (X) by reacting with 2-bromomethyl-3-ethoxycarbonylpyridine in an inert organic solvent, e.g. acetonitrile in the presence of an acid scavenger e.g. potassium carbonate. A period of one or two days under reflux may be necessary to complete reaction and the product is then isolated and purified by conventional techniques.

(j) The compounds of formula (I) wherein X is a 1-(5cyano-3-methylpyrimidine-2,4-dione) group are prepared from the corresponding 2-(aminoalkoxymethyl)-1,4-dihydropyridines (X) by reaction with 2-cyano-N-ethoxycarbonyl-2-ethoxymethylene-N-methylacetamide in a lower alkanol solvent in the presence of a trace of base. A period of 2 or 3 hours refluxing in methanol is generally sufficient.

(k) The compounds of formula (I) wherein X is a 1-(dihydro-pyrrol-2,5-dione) group are prepared from the corresponding 2-(aminoalkoxymethyl)-1,4-dihydropyridines (X) by reacting with maleic anhydride in an inert organic solvent e.g. acetonitrile under reflux for one or two hours.

The ability of the compounds to inhibit the movement of calcium into the cell is shown by their effectiveness in reducing the response of isolated heart tissue to an increase in calcium ion concentration in vitro. The test is performed by mounting spirally cut strips of rat aorta with one end fixed and the other attached to a force transducer. The tissue is immersed in a bath of physiological saline solution containing potassium ions at a concentration of 45 millimolar and no calcium. Calcium chloride is added to the bath with a pipette to give a final calcium ion concentration of 2 millimolar. The change in tension caused by the resulting contraction of the tissue is noted. The bath is drained and replaced with fresh saline solution and after 45 minutes, the procedure is repeated with the particular compound under test present in the saline solution. The concentration of compound required to reduce the response by 50% is recorded.

The antihypertensive activity of the compounds is also evaluated after oral administration by measuring the fall in blood pressure in spontaneously hypertensive rats or renally hypertensive dogs.

For administration to man in the curative or prophylactic treatment of cardiac conditions and hypertension, oral dosages of the compounds will generally be in the range of from 2–100 mg daily for an average adult patient (70 kg). Thus for a typical adult patient, individual tablets or capsules contain from 1 to 10 mg of active compound, in a suitable pharmaceutically acceptable vehicle or carrier. Dosages for intravenous administration would typically be within the range 1 to 10 mg per single dose as required. In practice the physician will determine the actual dosage which will be most suitable for an individual patient and it will vary with the age, weight and response of the particular patient. The above dosages are exemplary of the average case but there can, of course, be individual instances where higher or lower dosage ranges are merited, and such are within the scope of this invention.

For human use, the compounds of the formula (I) can be administered alone, but will generally be administered in admixture with a pharmaceutical carrier selected with regard to the intended route of administration and standard pharmaceutical practice. For example, they may be administered orally in the form of tablets containing such excipients as starch or lactose, or in capsules or ovules either alone or in admixture with excipients, or in the form of elixirs or suspensions containing flavouring or colouring agents. They may be injected parenterally, for example, intravenously, intramuscularly or subcutaneously. For parenteral administration, they are best used in the form of a sterile aqueous solution which may contain other substances, for example, enough salts or glucose to make the solution isotonic with blood.

Thus in a further aspect the invention provides a pharmaceutical composition comprising a compound of the formula (I), or a pharmaceutically acceptable salt thereof, together with a pharmaceutically acceptable diluent or carrier.

The invention also provides a compound of the formula (I) or a pharmaceutically acceptable salt thereof, for use in the treatment of cardiovascular conditions including use in the prevention or treatment of cardiac conditions, or use as an antihypertensive, in man.

The preparation of the compounds of the invention is illustrated by the following Examples.

EXAMPLE 1

2-Amino-6-{[4-(2-chlorophenyl)-3-ethoxycarbonyl-5-methoxycarbonyl-6-methyl-1,4-dihydropyridin-2-yl]methoxymethyl}-4-pyrimidone A solution of guanidine hydrochloride (0.20 g), ethyl 4-{[4-(2-chlorophenyl)-3-ethoxycarbonyl-5-methoxycarbonyl-6-methyl-1,4-dihydropyridin-2-yl]methoxy}acetoacetate (0.99 g), and 1,5-diazabicyclo[4.3.0]non-5-ene (0.30 g) in ethanol (50 ml) was stirred at room temperature for 5 days and then evaporated. The residue was dissolved in chloroform and washed with 2M hydrochloric acid, 10% aqueous sodium carbonate, and water, dried (MgSO$_4$), and evaporated. The residual solid was recrystallised from ethyl acetate to give the title compound (0.23 g), m.p. 185°–187° C. Found: C,56.08; H,5.14; N,11.33. C$_{23}$H$_{25}$ClN$_4$O$_6$ requires C,56.50; H,5.15; N,11.46%.

EXAMPLE 2

2-Amino-6-{[4-(2,3-dichlorophenyl)-3-ethoxycarbonyl-5-methoxycarbonyl-6-methyl-1,4-dihydropyridin-2-yl]methoxymethyl}-4-pyrimidone A solution of ethyl 4-{[4-(2,3-dichlorophenyl)-3-ethoxycarbonyl-5-methoxycarbonyl-6-methyl-1,4-dihydropyridin-2-yl]methoxy}acetoacetate (0.74 g), 1,5-diazabicyclo[4.3.0]non-5-ene (0.25 g) and guanidine hydrochloride (0.14 g) in ethanol (30 ml) was heated under reflux for 5.5 hours and then evaporated. The residue was dissolved in chloroform and the solution washed successively with water, 10% aqueous sodium carbonate solution and water, dried over anhydrous magnesium sulphate and evaporated. The residue was triturated with ethyl acetate and the resulting precipitate collected, washed thoroughly with diethyl ether, recrystallized from ethyl acetate/ethanol and dried to give the title compound (0.20 g), m.p. 222°–225° C. Found: C,52.10; H,4.56; N,10.54. C$_{23}$H$_{24}$Cl$_2$N$_4$O$_6$ requires C,52.78; H,4.62; N,10.70%.

EXAMPLES 3–12

The following compounds were prepared by the method of process (c) as described in Example 1 or 2 by reacting the appropriate 4-(1,4-dihydropyridine-2-ylmethoxy)acetoacetate of formula (VI) with the appropriate amidine or guanidine of formula (VIa).

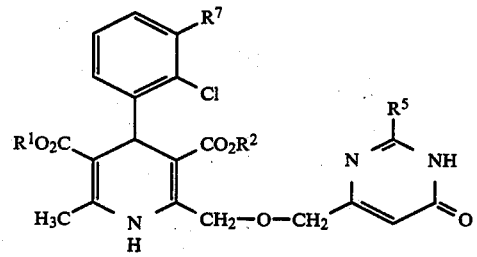

| Example No. | R$^1$ | R$^2$ | R$^7$ | R$^5$ | m.p. (°C.) | Form Characterised | Analysis % (Theoretical in brackets) | | |
|---|---|---|---|---|---|---|---|---|---|
| | | | | | | | C | H | N |
| 3 | CH$_3$ | C$_2$H$_5$ | H | CH$_3$ | 230–235 (decomp.) | hemihydrate | 58.31 (58.00) | 5.41 5.48 | 8.32 8.45) |
| 4 | CH$_3$ | C$_2$H$_5$ | Cl | CH$_3$ | 225–230 | hydrate | 53.64 (53.34) | 4.70 5.03 | 7.91 7.77) |
| 5 | C$_2$H$_5$ | CH$_3$ | Cl | NH$_2$ | 220 | hydrate | 51.02 (51.02) | 4.67 4.47 | 10.53 10.35) |
| 6 | CH$_3$ | C$_2$H$_5$ | CF$_3$ | NH$_2$ | 228–229 | hemihydrate | 50.96 (50.93) | 4.41 4.45 | 10.02 9.90) |
| 7 | C$_2$H$_5$ | CH$_3$ | CF$_3$ | NH$_2$ | 220 | hydrate | 50.17 (50.13) | 4.48 4.56 | 9.63 9.74) |
| 8 | CH$_3$ | C$_2$H$_5$ | H | C$_6$H$_5$ | 196–198 | free base | 62.71 (63.32) | 5.18 5.13 | 7.50 7.64) |
| 9 | CH$_3$ | C$_2$H$_5$ | Cl | N(CH$_3$)$_2$ | 219–222 | free base | 54.13 (54.45) | 5.18 5.12 | 9.90 10.16) |

-continued

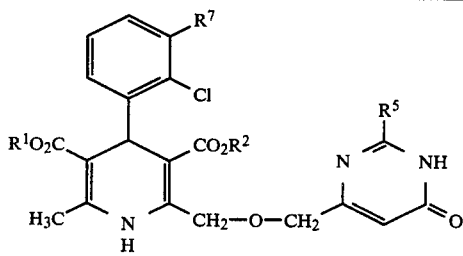

| Example No. | $R^1$ | $R^2$ | $R^7$ | $R^5$ | m.p. (°C.) | Form Characterised | Analysis % (Theoretical in brackets) | | |
|---|---|---|---|---|---|---|---|---|---|
| | | | | | | | C | H | N |
| 10 | $CH_3$ | $C_2H_5$ | H | morpholinyl | 151–155 | free base | 57.02 (58.01 | 5.56 5.59 | 10.08 10.02) |
| 11 | $CH_3$ | $C_2H_5$ | Cl | piperidinyl | 147–150 | free base | 56.85 (56.85 | 5.65 5.45 | 9.34 9.47) |

EXAMPLE 12

2-Amino-6-{[4-(2,3-dichlorophenyl)-3-ethoxycarbonyl-5-methoxycarbonyl-6-methyl-1,4-dihydropyridin-2-yl]methoxymethyl}-3-methyl-4-pyrimidone A mixture of 2-amino-6-{[4-(2,3-dichlorophenyl)-3-ethoxycarbonyl-5-methoxycarbonyl-6-methyl-1,4-dihydropyridin-2-yl]methoxymethyl}-4-pyrimidone (0.52 g), iodomethane (0.14 g) and potassium carbonate (0.14 g) in dimethylformamide (20 ml) was stirred at room temperature for 4 days and then evaporated. The residue was partitioned between chloroform and water and the organic layer washed twice with water, dried over anhydrous magnesium sulphate and evaporated. The residue was crystallised from ethyl acetate to give the title compound (0.23 g), m.p. 202°–205° C. Found: C,53.42; H,4.87; N,10.49. $C_{24}H_{26}Cl_2N_4O_6$ requires C,53.64; H,4.88; N,10.43%.

EXAMPLE 13

6-{[4-(2,3-Dichlorophenyl)-3-ethoxycarbonyl-5-methoxycarbonyl-6-methyl-1,4-dihydropyridin-2-yl]methoxymethyl}-2,3-dimethyl-4-pyrimidone was prepared by the method described in Example 12 using 6-{[4-(2,3-dichlorophenyl)-3-ethoxycarbonyl-5-methoxycarbonyl-6-methyl-1,4-dihydropyridin-2-yl]methoxymethyl}-2-methyl-4-pyrimidone as the starting material. The product had
m.p. 153°–158° C. Found: C,55.66; H,5.09; N,7.97. $C_{25}H_{27}Cl_2N_3O_6$ requires C,55.98; H,5.07; N,7.83%.

EXAMPLE 14

7-{[4-(2,3-Dichlorophenyl)-3-ethoxycarbonyl-5-methoxycarbonyl-6-methyl-1,4-dihydroopyridin-2-yl]methoxymethyl}-5-hydroxyimidazo[1,2-a]pyridimidine A mixture of 2-aminoimidazolium sulphate (0.52 g), ethyl 4-{[4-(2,3-dichlorophenyl)-3-ethoxycarbonyl-5-methoxycarbonyl-6-methyl-1,4-dihydropyridin-2-yl]methoxy}acetoacetate (1.50 g) and 1,5-diazabicyclo[4.3.0]non-5-ene (1.06 g) in ethanol (40 ml) was heated under reflux for 3.5 hours and then evaporated. The residue was partitioned between chloroform and water and the organic layer washed three times with water, dried over anhydrous magnesium sulphate and evaporated. The residue was purified by chromatography on silica gel (3 g) using chloroform plus 0–1% by volume of methanol as eluant. Appropriate fractions were combined and evaporated and the residue crystallised from ethyl acetate to give the title compound (0.28 g), m.p. 187°–188° C. Found: C,54.78; H,4.64; N,10.42. $C_{25}H_{24}Cl_2N_4O_6$ requires C,54.85; H,4.42; N,10.24%.

EXAMPLE 15

The following compound was prepared by the method described in Example 14 using 2-iminopiperidine as the starting material.

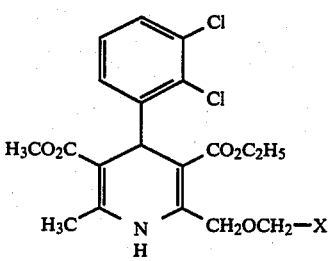

| Example No. | X | m.p. (°C.) | Analysis % (Theoretical in Brackets) | | |
|---|---|---|---|---|---|
| | | | C | H | N |
| 15 | [piperidine-pyrimidinone structure] | 177–8 | 54.13 (54.45 | 5.18 5.12 | 9.90 10.16) |

EXAMPLE 16

5-{[4-(2-Chlorophenyl)-3-ethoxycarbonyl-5-methoxycarbonyl-6-methyl-1,4-dihydropyridin-2-yl]methoxymethyl}-3-pyrazolone A solution of ethyl 4-{[4-(2-chlorophenyl)-3-ethoxycarbonyl-5-methoxycarbonyl-6-methyl-1,4-dihydropyridin-2-yl]methoxy}acetoacetate (0.50 g) and hydrazine hydrate (0.50 g) in ethanol (20 ml) was kept at room temperature for 4 days and then evaporated. The residue was purified by chromatography on silica gel (1.0 g) using dichloromethane plus 0–5% by volume of methanol as eluant. Appropriate fractions were combined and evaporated and the residue crystallised from ethyl acetate to give the title compound (0.18 g), m.p. 207° C. Found: C,57.11; H,5.15; N,9.19. $C_{22}H_{24}ClN_3O_6$ requires: C,57.20; H,5.24; N,9.10%.

EXAMPLE 17

2-Amino-1-<2-{[4-(2,3-dichlorophenyl)-3-ethoxycarbonyl-5-methoxycarbonyl-6-methyl-1,4-dihydropyridin-2-yl]methoxy}ethyl>-4-imidazolone A solution of 2-{2-[(N-cyano-N-ethoxycarbonylmethyl)amino]ethoxymethyl}-4-(2,3-dichlorophenyl)-3-ethoxycarbonyl-5-methoxycarbonyl-6-methyl-1,4-dihydropyridine (0.70 g) in saturated methanolic ammonia (10 ml) was stirred at room temperature for 16 hours and then evaporated. The residual solid was recrystallised from ethanol to give the title compound as a hemihydrate (0.46 g), m.p. 134°–138° C. Found: C,51.83; H,5.27; N,10.02. $C_{23}H_{26}Cl_2N_4O_6.0.5H_2O$ requires: C,51.68; H,5.06; N,10.48%.

EXAMPLE 18

2-Amino-1-<2-{[4-(2-chlorophenyl)-3-ethoxycarbonyl-5-methoxycarbonyl-6-methyl-1,4-dihydropyridin-2-yl]methoxy}ethyl>-4-imidazolone was prepared by the method described in Example 17 using 4-(2-chlorophenyl)-2-{2-[(N-cyano-N-ethoxycarbonylmethyl)amino]ethoxymethyl}-3-ethoxycarbonyl-5-methoxycarbonyl-6-methyl-1,4-dihydropyridine as the starting material. The product was characteised as its hemihydrate, m.p. 110°–113° C. Found: C,55.45; H,5.56; N,11.20. $C_{23}H_{27}ClN_4O_6.0.5H_2O$ requires: C,55.20; H,5.60; N,11.20%.

EXAMPLE 19

1-<2-{[4-(2-Chlorophenyl)-3-ethoxycarbonyl-5-methoxycarbonyl-6-methyl-1,4-dihydropyridin-2-yl]methoxy}ethyl>imidazolidine-2,5-dione A solution of 1-<2-{[4-(2-chlorophenyl)-3-ethoxycarbonyl-5-methoxycarbonyl-6-methyl-1,4-dihydropyridin-2-yl]methoxy}ethyl>-3-(ethoxycarbonylmethyl)urea (1.08 g) in methanol (1 ml) and 0.880 aqueous ammonia (2 ml) was stirred at room temperature for 16 hours and then evaporated. The residue was purified by chromatography on silica (2.5 g) using chloroform plus 0–5% v/v methanol as eluant. Appropriate fractions were combined and evaporated and the residual solid recrystallised from a mixture of ethyl acetate and acetone to give the title compound (0.20 g), m.p. 140° C. Found: C,56.17; H,5.64; N,8.45. $C_{23}ClN_3O_7$ requires C,56.15; H,5.33; N,8.54%.

EXAMPLE 20

1-<2-{[4-(2-Chlorophenyl)-3-ethoxycarbonyl-5-methoxycarbonyl-6-methyl-1,4-dihydropyridin-2-yl]methoxy}ethyl>imidazolidine-2,4-dione Sodium hydride (60 mg; 80% dispersion in oil) was added to a suspension of 1->2-{[4-(2-chlorophenyl)-3-ethoxycarbonyl-5-methoxycarbonyl-6-methyl-1,4-dihydropyridin-2-yl]methoxy}ethyl>-1-(methoxycarbonylmethyl)urea (0.52 g) in methanol (40 ml) and the mixture stirred at room temperature for one hour. The reaction mixture was evaporated and the residue partitioned between ethyl acetate and water. The organic layer was dried ($MgSO_4$) and evaporated and the residue triturated with diethyl ether. The resulting solid was collected, washed with diethyl ether and dried to give the title compound (0.41 g), m.p. 105°–107° C. (decomp.). Found: C,56.20; H,5.50; N,8.36. $C_{23}H_{26}ClN_3O_7$ requires: C,56.16; H,5.33; N,8.54%.

EXAMPLES 21–27

The following compounds were prepared by the method described in Example 20 using the appropriate starting materials of formula (VIII) and were characterised in the form indicated.

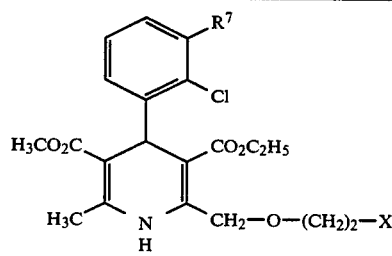

| Example No. | R[7] | X | Form characterised | m.p. (°C.) | Analysis % (Theoretical in brackets) | | |
|---|---|---|---|---|---|---|---|
| | | | | | C | H | N |
| 21 | Cl | -N⟨(C=O)NH(C=O)CH₂⟩ (hydantoin) | free base, hemihydrate | 116–118 | 51.69 (51.60 | 4.99 4.86 | 7.79 7.85) |
| 22 | H | -N⟨(C=O)NCH₃(C=O)CH₂⟩ | free base | 166–167 | 56.65 (56.97 | 5.59 5.58 | 8.25 8.31) |
| 23 | Cl | -N⟨(C=O)NCH₃(C=O)CH₂⟩ | free base, hemihydrate | 115–116 | 52.44 (52.45 | 4.94 5.10 | 7.51 7.65) |
| 24 | H | -N⟨(C=O)NH–C(NH₂)=CH⟩ | free base, hydrate | 132–134 | 54.73 (54.28 | 5.51 5.70 | 11.17 11.01) |
| 25 | Cl | -N⟨(C=O)NH–C(NH₂)=CH⟩ | hydrochloride, dihydrate | 131–133 | 46.73 (46.54 | 4.67 5.23 | 9.63 9.44) |
| 26 | H | -N⟨(C=O)NH–CH=C(NH₂)⟩ | hydrochloride, dihydrate | 138–139 | 49.64 (49.46 | 5.44 5.55 | 10.21 10.04) |
| 27 | H | -N⟨(C=O)NCH₃–C(CH₃)₂(C=O)⟩ (with extra O) | free base, sesquihydrate | 117–119 | 56.76 (56.66 | 5.89 6.10 | 7.29 7.32) |

EXAMPLE 28

1-<2-{[4-(2-Chlorophenyl)-3-ethoxycarbonyl-5-methoxycarbonyl-6-methyl-1,4-dihydropyridin-2-yl]methoxy}ethyl>-2-methyl-5-imidazolone A solution of 2-(2-aminoethoxy)methyl-3-ethoxycarbonyl-5-methoxycarbonyl-6-methyl-1,4-dihydropyridine (1.02 g) and ethyl N-(ethoxycarbonylmethyl)acetimidate (0.43 g) in ethanol (20 ml) was stirred at room temperature for 16 hours and then evaporated. The residue was purified by chromatography on silica (10 g) using dichloromethane plus 0–5% v/v methanol as eluant. Appropriate fractions were combined and evaporated to give the title compound (0.07 g), m.p. 167°-169° C. Found: C,58.30; H,5.79; N,8.55. C$_{24}$H$_{28}$ClN$_3$O$_6$ requires: C,58.83; H,5.72; N,8.58%.

EXAMPLE 29

1-<2-{[4-(2-Chlorophenyl)-3-ethoxycarbonyl-5-methoxycarbonyl-6-methyl-1,4-dihydropyridin-2-yl]methoxy}ethyl>-2-pyridone A solution of 1-(2-hydroxyethyl)-2-pyridone (6.15 g) in tetrahydrofuran (30 ml) was added over 45 minutes to a suspension of sodium hydride (3.0 g; 80% dispersion in oil) in tetrahydrofuran (30 ml). The mixture was stirred at room temperature for one hour, treated with a solution of ethyl 4-chloroacetoacetate (8.23 g) in tetrahydrofuran (20 ml) dropwise over 3 hours and then stirred at room temperature for 16 hours. The reaction mixture was reacted with ethanol (10 ml), poured into concentrated hydrochloric acid (10 ml) and extracted into ethyl acetate. The ethyl acetate extract was dried (MgSO$_4$) and evaporated to give ethyl 4-[2-(2-pyridon-1-yl)ethoxy]acetoacetate as a brown oil which was shown by n.m.r. to be 75% pure. A solution of this crude product (5.4 g) and ammonium acetate (1.50 g) in ethanol (20 ml) was heated at 50° C. for 30 minutes, treated with methyl 2-(2-chlorobenzylidene)acetoacetate (3.57 g) and the mixture heated under reflux for 3 hours. The reaction mixture was evaporated and the residue dissolved in toluene, washed with 2M hydrochloric acid, dried (MgSO$_4$) and evaporated. The residue was purified by chromatography on silica (50 g) using petroleum ether (b.p. 40°-60° C.) plus 70-100% v/v dichloromethane as eluant. Appropriate fractions were combined and evaporated to give the title compound (0.15 g), m.p. 114°-115° C. Found: C,61.66; H,5.55; N,5.75. C$_{25}$H$_{27}$ClN$_2$O$_6$ requires C,61.37; H,5.65; N,5.70%.

EXAMPLES 30 AND 31

The following compounds were prepared by the method described in Example 29 using the appropriate starting materials of formulae (IV) and (V) and were characterised in the form indicated.

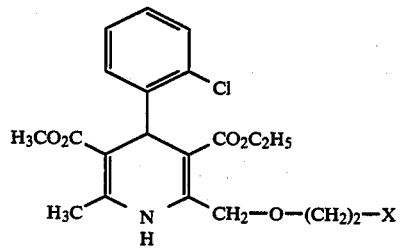

| Example No. | X | Form characterised | m.p. (°C.) | Analysis % (Theoretical in brackets) | | |
|---|---|---|---|---|---|---|
| | | | | C | H | N |
| 30 | (piperazin-2-one) | dihydrochloride hydrate | 90 | 49.95 (49.45 | 5.93 5.88 | 7.31 7.21) |
| 31 | (theophyllinyl) | free base | 152-153 | 53.06 (53.47 | 4.86 4.82 | 11.42 11.55) |

EXAMPLE 32

1-<2-{[4-(2-Chlorophenyl)-3-ethoxycarbonyl-5-methoxycarbonyl-6-methyl-1,4-dihydropyridin-2-yl]methoxy}ethyl>-4-ethoxycarbonyl-5-hydroxy-(1H)-1,2,3-triazole A mixture of 2-(2-azidoethoxy)methyl-4-(2-chlorophenyl)-3-ethoxycarbonyl-5-methoxycarbonyl-6-methyl-1,4-dihydropyridine (2.17 g), diethyl malonate (4.00 g) and sodium hydride (0.75 g; 80% dispersion in oil) in ethanol (80 ml) was heated under reflux for 16 hours and then evaporated. The residue was partitioned between 0.1M hydrochloric acid and ethyl acetate and the organic layer was washed with water, dried (Na$_2$SO$_4$) and evaporated. The residue was triturated with ether and the resulting solid collected and purified by chromatography on silica (30 g) using dichloromethane plus 0-5% v/v methanol as eluant. Appropriate fractions were combined and evaporated to give the title compound (0.89 g), m.p. 121°-124° C. Found: C,55.01; H,5.49; N,10.07. C$_{25}$H$_{29}$ClN$_4$O$_8$ requires: C,54.69; H,5.32; N,10.21%.

EXAMPLE 33

2-<2-{[4-(2,3-Dichlorophenyl)-3-ethoxycarbonyl-5-methoxycarbonyl-6-methyl-1,4-dihydropyridin-2-yl]methoxy}ethyl>-1-oxo-1,3-dihydropyrrolo[2,3-b]pyridine A mixture of 2-(2-aminoethoxy)methyl-4-(2,3-dichlorophenyl)-3-ethoxycarbonyl-5-methoxycarbonyl-6-methyl-1,4-dihydropyridine (0.50 g), 2- bromomethyl-3-ethoxycarbonylpyridine (0.31 g) and potassium carbonate (0.56 g) in acetonitrile (30 ml) was heated under reflux for 41 hours, filtered and evaporated. The residue was purified by chromatography on silica (10 g) using dichloromethane plus 0–5% v/v methanol as eluant. Appropriate fractions were combined and evaporated and the residue triturated with ether. The resulting solid was collected, washed with ether and dried to give the title compound (0.22 g), m.p. 147°–149° C. Found: C,57.96; H,5.07; N,7.47. $C_{27}H_{27}Cl_2N_3O_6$ requires C,57.86; H,4.86; N,7.50%.

EXAMPLE 34

5-Cyano-1-<2-{[4-(2-chlorophenyl)-3-ethoxycarbonyl-5-methoxycarbonyl-6-methyl-1,4-dihydropyridin-2-yl]methoxy}ethyl>-3-methylpyrimidine-2,4-dione A solution of 2-(2-aminoethoxy)methyl-4-(2-chlorophenyl)-3-ethoxycarbonyl-5-methoxycarbonyl-6-methyl-1,4-dihydropyridine (0.82 g) and 2-cyano-N-ethoxycarbonyl-2-ethoxymethylene-N-methylacetamide (0.5 g) in methanol (2 ml) containing one drop of triethylamine was heated under reflux for 2 hours, diluted with toluene (5 ml) and evaporated. The residue was purified by chromatography on silica (5 g) using toluene plus 0–100% v/v chloroform as eluant. Appropriate fractions were combined and evaporated and the residue crystallised from a mixture of ethyl acetate and diethyl ether. The resulting solid was collected and recrystallised from a mixture of acetone and diisopropyl ether to give the title compound (0.25 g), m.p. 155°–156° C. Found: C,57.46; H,5.09; N,10.13. $C_{26}H_{27}ClN_4O_7$ requires: C,57.50; H,5.03; N,10.32%.

EXAMPLE 35

1-<2-{[4-(2-Chlorophenyl)-3-ethoxycarbonyl-5-methoxycarbonyl-6-methyl-1,4-dihydroopyridin-2-yl]methoxy}-ethyl>maleimide A solution of 2-(2-aminoethoxy)methyl-4-(2-chlorophenyl)-3-ethoxycarbonyl-5-methoxycarbonyl-6-methyl-1,4-dihydropyridine (0.82 g) and maleic anhydride (0.25 g) in acetonitrile (2 ml) was heated under reflux for 50 minutes, treated with acetic anhydride (1 ml), heated under reflux for a further one hour, diluted with methanol (2 ml), heated under reflux for a further 20 minutes and evaporated. The residue was partitioned between ethyl acetate and 10% aqueous sodium carbonate and the organic layer dried ($Na_2CO_3$) and evaporated. The residue was purified by chromatography on silica (3 g) using toluene plus 0–100% v/v chloroform as eluant. Appropriate fractions were combined and evaporated and the residue triturated with diethyl ether. The resulting solid was collected and recrystallised from a mixture of acetone and diisopropyl ether to give the title compound (0.18 g), m.p. 140°–141° C. Found: C,58.77; H,5.16; N,5.85. $C_{24}H_{25}ClN_2O_7$ requires: C,58.95; H,5.15; N,5.73%.

EXAMPLE 36

Tablets are compounded from the following ingredients:

| | mg/tablet |
|---|---|
| Product of any one of Examples | 10 |
| Dicalcium phosphate | 120 |
| Magnesium stearate | 1.8 |
| Sodium lauryl sulphate | 0.2 |

The ingredients are thoroughly blended, compressed, granulated and recompressed to tablets of the desired size.

EXAMPLE 37

Capsules are compounded from the following ingredients:

| | mg/capsule |
|---|---|
| Product of any one of Examples | 10 |
| Maize starch | 127 |
| Cellulose (microcrystalline) | 127 |
| Magnesium stearate | 5.4 |
| Sodium lauryl sulphate | 0.6 |

The ingredients are thoroughly blended, then filled into hard gelatine capsules of the appropriate size to contain the ingredients.

PREPARATION 1

Ethyl 4-{[4-(2-chlorophenyl)-3-ethoxycarbonyl-5-methoxycarbonyl-6-methyl-1,4-dihydropyridin-2-yl]methoxy}acetoacetate A solution of 2-{[4-(2-chlorophenyl)-3-ethoxycarbonyl-5-methoxycarbonyl-6-methyl-1,4-dihydropyridin-2-yl]methoxy}acetic acid (4.24 g) in tetrahydrofuran (60 ml) was treated with ice-cooling with carbonyldiimidazole (1.70 g) and the mixture stirred at 0° C. for 2.25 hours. This solution was added dropwise over 10 minutes to a solution of the sodium salt of 2,2-dimethyl-1,3-dioxane-4,6-dione in dimethylformamide (prepared by stirring a mixture of 2,2-dimethyl-1,3-dioxane-4,6-dione (1.44 g) and sodium hydride (0.30 g; 80% dispersion in oil) in dimethylformamide (30 ml) with ice-cooling for 30 minutes) and the mixture stirred for 16 hours at room temperature and then evaporated. The residue was dissolved in dichloromethane, washed twice with 1M hydrochloric acid and water, dried ($MgSO_4$), and evaporated. A solution of the residual oil (6 g) in ethanol (50 ml) was heated under reflux for 6 hours and evaporated. The residue was dissolved in diethyl ether, washed twice with 10% aqueous sodium carbonate and once with saturated aqueous sodium chloride, dried ($MgSO_4$), and evaporated. The residue was purified by chromatography on silica (30 g) using hexane plus 5–15% v/v ethyl acetate as eluant. Appropriate fractions were combined and evaporated and the residue crystallised from ethanol to give the title compound (1.5 g), m.p. 88°–89° C. Found: C,58.18; H,5.73; N,2.85. $C_{24}H_{28}ClNO_8$ requires: C,58.36; H,5.71; N,2.84%.

PREPARATION 2

Ethyl 4-{[4-(2,3-dichlorophenyl)-3-ethoxycarbonyl-5-methoxycarbonyl-6-methyl-1,4-dihydropyridin-2-yl]methoxy}acetoacetate A solution of carbonyl diimidazole (5.20 g) and 2-{[4-(2,3-dichlorophenyl)-3-ethoxycarbonyl-5-methoxycarbonyl-6-methyl-1,4-dihydropyridin-2-yl]methoxy}acetic acid (14.00 g) in dichloromethane (200 ml) was stirred at room temperature under nitrogen for 2 hours and then added to a solution of pyridine (2.40 g) and 2,2-dimethyl-1,3-dioxane-4,6-dione (4.56 g) in dichloromethane (200 ml) over 8 minutes. The mixture was stirred at room temperature for 2.5 hours, washed successively with water, ice-cold 2.5M hydrochloric acid and saturated brine, dried over anhydrous magnesium sulphate and evaporated. The residue was dissolved in ethanol (200 ml) and the solution heated under reflux for 2.75 hours and evaporated. The residue was triturated with diethyl ether and the resulting solid collected washed with diethyl ether and dried to give the title compound (9.0 g), m.p. 99°–102° C.

PREPARATIONS 3–6

The following compounds were prepared by the method described in Preparations 1 and 2 from the appropriate 2-(dihydropyridin-2-ylmethoxy)acetic acid.

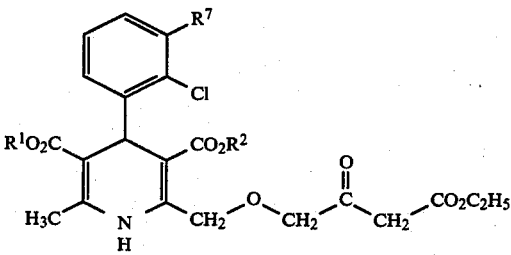

| Preparation No. | $R^1$ | $R^2$ | $R^7$ | m.p. (°C.) | C | H | N |
|---|---|---|---|---|---|---|---|
| 3 | CH$_3$ | CH$_2$CH$_3$ | Cl | 99–102 | characterised by $^1$H—n.m.r. | | |
| 4 | CH$_2$CH$_3$ | CH$_3$ | Cl | 134–7 | 54.44 (54.55) | 5.21 (5.15) | 2.64 (2.65) |
| 5 | CH$_3$ | CH$_2$CH$_3$ | CF$_3$ | 96 | characterised by $^1$H—n.m.r. | | |
| 6 | CH$_2$CH$_3$ | CH$_3$ | CF$_3$ | 125–8 | 53.04 (53.43) | 4.80 (4.84) | 2.44 (2.49) |

PREPARATION 7

2-{2-[(N-Cyano-N-ethoxycarbonylmethyl)amino]ethoxymethyl}-4-(2-chlorophenyl)-3-ethoxycarbonyl-5-methoxycarbonyl-6-methyl-1,4-dihydropyridine Cyanogen bromide (0.35 g) was added to a stirred solution of 4-(2-chlorophenyl)-3-ethoxycarbonyl-2-{2-[(N-ethoxycarbonylmethyl)amino]amino]ethoxymethyl}-5-methoxycarbonyl-6-methyl-1,4-dihydropyridine (1.25 g) in chloroform (10 ml) containing sodium hydrogen carbonate (0.3 g). The mixture was stirred at room temperature for 20 hours and then evaporated. The residue was triturated with diethyl ether and the resulting solid collected, washed with diethyl ether and dried to give the title compound as a hemihydrate (0.81 g), m.p. 132°–134° C. Found: C,56.96; H,5.66; N,7.94. C$_{25}$H$_{30}$ClN$_3$O$_7$.0.5H$_2$O requires: C,56.76; H,5.86; N,7.94%.

PREPARATION 8

2-{2-[(N-Cyano-N-ethoxycarbonylmethyl)amino]ethoxymethyl-4-(2,3-dichlorophenyl)-3-ethoxycarbonyl}-5-methoxycarbonyl-6-methyl-1,4-dihydropyridine was prepared by the method described in Preparation 7 using 4-(2,3-dichlorophenyl)-3-ethoxycarbonyl-2-{2-[(N-ethoxycarbonylmethyl)amino]ethoxymethyl}-5-methoxycarbonyl-6-methyl-1,4-dihydropyridine as the starting material. The product was obtained as a hemihydrate, m.p. 148°–150° C. Found: C,53.08; H,5.04; N,7.46. C$_{25}$H$_{29}$Cl$_2$N$_3$O$_7$.0.5H$_2$O requires: C,53.28; H,5.33; N,7.46%.

PREPARATION 9

1-<2-{[4-(2-Chlorophenyl)-3-ethoxycarbonyl-5-methoxycarbonyl-6-methyl-1,4-dihydropyridin-2-yl]methoxy}ethyl>-3-(cyanomethyl)urea A solution of 4-(2-chlorophenyl)-3-ethoxycarbonyl-2-{2-[N-(1-imidazolylcarbonyl)amino]ethoxymethyl}-5-methoxycarbonyl-6-methyl-1,4-dihydropyridine (0.98 g), aminoacetonitrile hydrochloride (0.30 g) and N-methylmorpholine (0.44 g) was stirred at room temperature for 20 hours and then evaporated. The residue was purified by chromatography on silica (10 g) using dichloromethane plus 0–5% v/v methanol as eluant. Appropriate fractions were combined and evaporated and the residual solid recrystallised from ethanol to give the title compound as a hemihydrate (0.50 g), m.p. 145°–147° C. Found: C,55.34; H,5.84; N,11.33. C$_{23}$H$_{27}$ClN$_4$O$_6$.0.5H$_2$O requires: C,55.25; H,5.60; N,11.21%.

PREPARATION 10

4-(2-Chlorophenyl)-3-ethoxycarbonyl-2-{2-[N-(1-imidazolylcarbonyl)amino]ethoxymethyl}-5-methoxycarbonyl-6-methyl-1,4-dihydropyridine A solution of 2-(2-aminoethoxy)methyl-4-(2-chlorophenyl)-3-ethoxycarbonyl-5-methoxycarbonyl-6-methyl-1,4-dihydropyridine (20.4 g), carbonyldiimidazole (8.9 g) and N-methylmorpholine (20 ml) in tetrahydrofuran (500 ml) was stirred at room temperature for 2 hours and then evaporated. The residue was partitioned between ethyl acetate and water and the organic layer washed with water, dried (Na$_2$SO$_4$), and evaporated. The residual solid was washed with diethyl ether and dried to give the title compound (16.6 g), m.p. 149°–151° C. Found: C,57.35; H,5.54; N,11.22. C$_{24}$H$_{27}$ClN$_4$O$_6$ requires: C,57.54; H,5.43; N,11.18%.

PREPARATION 11

1-<2-{[4-(2-Chlorophenyl)-3-ethoxycarbonyl-5-methoxycarbonyl-6-methyl-1,4-dihydropyridin-2-yl]methoxy}ethyl>-1-(cyanomethyl)urea A mixture of 2-(2-aminoethoxy)methyl-4-(2-chlorophenyl)-3-ethoxycarbonyl-5-methoxycarbonyl-6-methyl-1,4-dihydropyridine (4.08 g), chloroacetonitrile (1.20 g), and potassium carbonate (1.20 g) in acetonitrile (40 ml) was heated under reflux for 16 hours and then evaporated. The residue was triturated with diethyl ether and the resulting solid dried and purified by chromatography on silica (40 g) using dichloromethane plus 0–5% v/v methanol as eluant. Appropriate fractions were combined and evaporated to give crude 4-(2-chlorophenyl)-2-[2-(N-cyanomethyl)amino-ethoxy]methyl-3-ethoxycarbonyl-5-methoxycarbonyl-6-methyl-1,4-dihydropyridine (2.0 g). Acetic acid (0.5 g) was added to a solution of the above product (1.0 g) and potassium cyanate (0.35 g) in water (15 ml) and dioxane (15 ml) and the mixture stirred at room temperature for 16 hours and then evaporated. The residue was partitioned between ethyl acetate and water and the organic layer dried (Na$_2$SO$_4$) and evaporated. The residue was purified by chromatography on silica (10 g) using dichloromethane plus 0–5% v/v methanol as eluant. Appropriate fractions were combined and evaporated to give the title compound (53 mg), m.p. 190°–191° C. Found: C,56.34; H,5.80; N,10.99. $C_{23}H_{27}ClN_4O_6$ requires: C,56.27; H,5.50; N,11.42%.

PREPARATION 12

1-<2-{[4-(2,3-Dichlorophenyl)-3-ethoxycarbonyl-5-methoxycarbonyl-6-methyl-1,4-dihydropyridin-2-yl]methoxy}ethyl>-1-(cyanomethyl)urea was prepared by the method described in Preparation 11 using 2-(2-aminoethoxy)methyl-4-(2,3-dichlorophenyl)-3-ethoxycarbonyl-5-methoxycarbonyl-6-methyl-1,4-dihydropyridine as starting material. The product was obtained as a foam. Rf (silica; chloroform, methanol, ammonium hydroxide; 80:20:1) 0.7.

We claim:

1. A 1,4-dihydropyridine compound having the formula

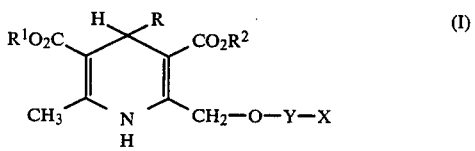

or a pharmaceutically acceptable salt thereof wherein

R is 2-chlorophenyl, 2,3-dichlorophenyl or 2-chloro-3-trifluoromethylphenyl; $R^1$ and $R^2$ are each independently $C_1$–$C_4$ alkyl;

X is a 4-pyrimidone bonded at the 6-position and substituted at the 2-position with amino, methyl, phenyl, dimethylamino, morpholino or piperidino and at the 3-position with hydrogen or methyl;

Y is —$(CH_2)_n$—;

and n is 1 to 2.

2. A compound according to claim 1 wherein R is 2-chlorophenyl or 2,3-dichlorophenyl.

3. A compound according to claim 2 wherein $R^1$ is $CH_3$ and $R^2$ is $C_2H_5$ and n is 1.

4. A compound according to claim 1 being 2-amino-6-{[4-(2,3-dichlorophenyl)-3-ethoxycarbonyl-5-methoxycarbonyl-6-methyl-1,4-dihydropyridin-2-yl]methoxymethyl}-4-pyrimidone.

5. A method for treating hypertension in a mammal in need of such treatment comprising the step of administering to said mammal an antihypertensive effective amount of a compound according to claim 1.

6. A method according to claim 5 wherein the compound is 2-amino-6-{[4-(2,3-dichlorophenyl)-3-ethoxycarbonyl-5-methoxycarbonyl-6-methyl-1,4-dihydropyridin-2-yl]methoxymethyl}-4-pyrimidone.

* * * * *